United States Patent [19]

Sanderson et al.

[11] Patent Number: 4,547,598

[45] Date of Patent: Oct. 15, 1985

[54] COBALT BORATE CATALYZED DECOMPOSITION OF ORGANIC HYDROPEROXIDES

[75] Inventors: John R. Sanderson, Austin; Kenneth P. Keating, Georgetown; Edward T. Marquis, Austin; Steven H. Vanderpool, New Braunfels, all of Tex.

[73] Assignee: Texaco, Inc., White Plains, N.Y.

[21] Appl. No.: 684,216

[22] Filed: Dec. 20, 1984

[51] Int. Cl.[4] .............................................. C07C 29/88
[52] U.S. Cl. .................................... 568/922; 502/202; 568/840
[58] Field of Search ........................... 568/922, 840 A

[56] References Cited

U.S. PATENT DOCUMENTS

| | | | |
|---|---|---|---|
| 2,570,216 | 10/1951 | Dice et al. ........................ | 568/910.5 |
| 2,700,677 | 1/1955 | Bowen et al. ...................... | 568/914 |
| 3,007,944 | 11/1961 | Amir ................................. | 568/910 |
| 3,336,390 | 8/1967 | Nelsen et al. ..................... | 568/912 |
| 3,470,239 | 9/1969 | Russell ............................. | 568/910 |
| 3,474,151 | 10/1969 | Grane ............................... | 568/913 |

*Primary Examiner*—J. E. Evans
*Attorney, Agent, or Firm*—Jack H. Park; Kenneth R. Priem

[57] ABSTRACT

A method for decomposing organic hydroperoxides to their corresponding alcohols is described. A solution containing the organic hydroperoxides is contacted with cobalt borate or cobalt borate on titanium dioxide catalyst. The hydroperoxide is reduced to at least 0.2 wt. % of the effluent and often less than 0.09 wt. %. Cobalt borate has the added advantage of not leaching cobalt into the effluent unlike known cobalt oxide decomposition catalysts.

9 Claims, No Drawings

COBALT BORATE CATALYZED DECOMPOSITION OF ORGANIC HYDROPEROXIDES

BACKGROUND OF THE INVENTION

1. Field of the Invention

The invention relates to methods for decomposing undesired organic hydroperoxides in liquid solutions and particularly relates to such decompositions which are catalytically promoted.

2. Other Methods in the Field

Organic hydroperoxides are useful materials, particularly as reactants in epoxidations. However, peroxides can also be very troublesome when present as undesirable components (by-products or leftover reactants) in ultimate product streams. For example, in techniques for oxidizing alkanes such as isobutane to give the corresponding alcohol, such as tertiary butyl alcohol for example, tertiary butyl hydroperoxide is also formed as an undesirable by-product. If the t-butyl alcohol is used as an anti-knock, anti-icing additive in gasoline, the t-butyl hydroperoxide must somehow be eliminated as it has an octane degrading effect.

Similarly, in methods for reacting olefins with organic hydroperoxides, there is usually some unreacted hydroperoxide remaining in the product effluent. Typically in such processes, large amounts of the alcohol corresponding to the hydroperoxide are also produced. If this alcohol is to be used in an application that is sensitive to the presence of even small amounts of residual hydroperoxide, as in the gasoline anti-knock, anti-icing additive noted above, the hydroperoxide must in some way be removed.

One technique for removing small quantities of hydroperoxide involves distilling off the hydroperoxide. This technique can be dangerous if it involves concentrating an unstable hydroperoxide. Molecular sieves are known to be effective in the removal of peroxides from contaminated ethers as revealed in D. R. Burfield, "Deperoxidation of Ethers. A Novel Application of Self-Indicating Molecular Sieves," *J. Org. Chem.*, 1982, Vol. 47, pp 3821–3824.

If the problem is one of removing hydroperoxide from a solution of its corresponding alcohol, the typical approach is to decompose or convert the hydroperoxide to the alcohol within the solution. One method of conducting this hydroperoxide decomposition is to treat the contaminated solution with high temperature. U.S. Pat. No. 3,474,151 to Grane teaches that hydroperoxides and peroxides contaminating t-butyl alcohol (TBA) product may be decomposed by subjecting the product to a temperature of from 375° F. to 475° F. for from 1 to 10 minutes. See also U.S. Pat. No. 4,294,999 to Grane, et al. (preferably 400°–450° F. for 5–9 minutes); U.S. Pat. No. 4,296,262 to Grane, et al. (280° F. for 10 hours) and U.S. Pat. No. 4,296,263 to Worrell (340° F. for 90 minutes).

Undesirable hydroperoxides have also been catalytically decomposed. Numerous acidic catalysts or soluble metal catalysts have been employed. Typically the catalysts or reactants employed are acids or ionized metal compounds in solution. The mechanism for acid and ionized metal-induced decomposition of hydroperoxides is discussed in Tobolsky, et al., *Organic Peroxides*, New York: Interscience, 1954, pp 57–122, and Davies, *Organic Peroxides*, London: Butterworths, 1961, pp 174–192.

It has also been taught that metals and compounds of metals of Groups IV-A, V-A or VI-A of the Periodic Chart, with the exception of chromium, catalyze the conversion of alkyenyl hydroperoxides to epoxy alcohols as taught in U.S. Pat. No. 3,505,360 to Allison, et al. Further, U.S. Pat. No. 4,059,598 to Coyle demonstrates the decomposition of residual hydroperoxides by contacting the product mixture with a heterogeneous cobalt oxide catalyst which may also contain copper oxide as a promoter. However, as will be shown, cobalt oxide, while it may be heterogeneous, is somewhat soluble in the product mixture. This result is undesirable because it diminishes the amount of available catalyst and because it futher contaminates the product with cobalt.

Therefore, an object of the invention is to provide a technique for organic hydroperoxide decomposition that does not involve a catalyst soluble to any measurable extent.

SUMMARY OF THE INVENTION

The invention concerns a method for the decomposition of an organic hydroperoxide which entails contacting a liquid solution containing an organic hydroperoxide with an insoluble cobalt borate catalyst to give an effluent substantially free of the organic hydroperoxide.

DETAILED DESCRIPTION OF THE PREFERRED EMBODIMENTS

It has been surprisingly discovered that cobalt borate is an effective and substantially insoluble catalyst for hydroperoxide decomposition. By "substantially insoluble" it is meant that after the decomposition reaction there is less than 0.2 ppm cobalt in the solution, 0.2 ppm representing the lowest detectable limit using our atomic adsorption analysis (AA). As will be demonstrated, other known catalysts, such as copper oxide promoted cobalt oxide, are soluble to some extent as determined by AA analysis for cobalt.

Cobalt borate, of the chemical formula $CoB_2O_4$, may be used alone or on an inert support. Generally, the support should be inert and neutral. Among the wide variety of suitable inert, non-acidic, inorganic supports which may be employed are: carbonaceous materials such as charcoal; normally insoluble inorganic salts such as barium sulfate; non-acidic crystalline aluminum silicates of the type known as molecular sieves and other inorganic oxides based on aluminum and/or silicon. A new support for cobalt borate has been found in the form of titanium dioxide and one of the preferred embodiments of this invention is cobalt borate on titanium dioxide ($TiO_2$).

As noted, the contaminated liquid solution may be a stream from the production of t-butyl alcohol from isobutane via catalytic oxidation or from the production of an alkylene oxide via olefin epoxidation, or other process, which contains an organic hydroperoxide as an undesired minor portion thereof, either as a by-product or as excess reactant. If the liquid solution contains from about 0.10 to 10.0 wt. % hydroperoxide, the concentration in the product effluent after treatment may be from 0.20 to as low as ~0.001 wt. % (or ~0%) hydroperoxide, preferably less than 0.09 wt. %, by iodometric titration.

The cobalt borate catalyst concentration may vary widely from 0.10 to 10.0 wt. % based on the solution to be treated. The preferred temperature range for this decomposition treatment is about 50° to 250° C., preferably 80° to 120° C. These temperatures are much lower than those used in thermal decomposition techniques. The decomposition of peroxide compounds according to this invention is generally effected in the liquid phase, by passing the mixture or solution through a suitably contained fixed bed of catalytic material or by contacting the reaction mixture with slurried catalyst.

A particularly preferred organic hydroperoxide known to be decomposed by this method is t-butyl hydroperoxide (TBHP). Most typically, TBHP will be present in a TBA stream from propylene oxide production. The TBHP has to be removed before TBA is used as a gasoline additive.

After the hydroperoxide-containing mixture has been treated by the method of this invention, the resultant stream, substantially free of hydroperoxides (0.2 wt. % or less) is separated to recover any remaining components thereof. Often, the hydroperoxide concentration in the effluent after treatment is less than 0.09 wt. %. Conventional methods, such as fractional distillation, selective extraction, filtration and the like may be used, depending on the type and amount of mixed components.

The following examples will further illustrate the method of this invention, but are not intended to limit the invention in any way. The hydroperoxide-containing solutions used throughout are mixtures of TBHP in TBA. It is anticipated that other components may be present without harm to the decomposition results.

EXAMPLES 1-18

A 250 ml round-bottomed flask equipped with a heating mantle, condenser and magnetic stirrer was charged with 50 ml of a dilute (2.15 wt. %) solution of t-butyl hydroperoxide in t-butyl alcohol. Catalyst was introduced and the mixture heated at 80° C. for 5 hours. The mixture was then cooled to ambient temperature and filtered through two pieces of fluted filter paper. Weight percent hydroperoxide was determined by iodometric titration. The metal content was determined by atomic adsorption. Results are shown in Table I.

In Example 1, a copper oxide-promoted cobalt oxide catalyst is used as taught in U.S. Pat. No. 4,059,598. The catalyst was useful for the decomposition of TBHP since only 0.020% remained in the treatment effluent. However, analysis of the filtered reaction mixture showed the presence of 0.24 ppm cobalt and 0.35 ppm copper, indicating that the catalyst was soluble in the reaction mixture.

In Example 6, a portion of the cobalt was recovered and used in Example 7. In Example 7, a portion of the catalyst was recovered and used in Example 8. The catalyst was still active after 15 hours. There was no loss of cobalt other than mechanical losses. Cobalt in solution (if any) was below detectable limits.

For Example 10, larger quantities of catalyst and solution were used. Aliquots were withdrawn at time intervals and the weight per cent t-butyl hydroperoxide determined. The results are shown in Table I.

TABLE I

| | Hydroperoxide Decompositions | | | | |
|---|---|---|---|---|---|
| Example | Catalyst | Grams | Wt. %[a] TBHP | Metal | ppm[b] |
| 1 | Cobalt Oxide-Copper Oxide | 0.50 | 0.02 | Co Cu | 0.24 0.35 |
| 2 | Ferric Borate | 0.52 | 1.69 | Fe | 0.43 |

TABLE I-continued

| | Hydroperoxide Decompositions | | | | |
|---|---|---|---|---|---|
| Example | Catalyst | Grams | Wt. %[a] TBHP | Metal | ppm[b] |
| 3 | Nickel Borate | 0.50 | 2.35 | Ni | <0.2 |
| 4 | Cobalt Borate | 0.22 | 0.16 | Co | 0.48 |
| 5 | Lithium Borate | 0.25 | 2.25 | Li | 4.14 |
| 6 | Cobalt Borate | 1.0 | 0.17 | Co | <0.2 |
| 7 | Cobalt Borate | 0.70 | 0.07 | Co | <0.2 |
| 8 | Cobalt Borate | 0.52 | 0.10 | Co | <0.2 |
| 9 | Silver on Copper Oxide | 0.52 | 0.51 | Ag Cu | 62.7 <0.2 |
| 10 | Cobalt Borate | 1.0 | 0.09 | Co | <0.2 |
| 11 | Silver on Alumina | 1.0 | 0.55 | Ag | 34.2 |
| 12 | Lithium Cobalt (III) Oxide | 0.50 | 1.39 | Li Co | 0.73 <0.2 |
| 13 | Cerium Oxide | 0.52 | 2.25 | — | — |
| 14 | Manganese (II, III) Oxide | 0.51 | 0.79 | Mn | 0.77 |
| 15 | Molybdenum Dioxide | 0.51 | 0.96 | Mo | 4530 |
| 16 | Cobalt Phosphate | 0.51 | 1.51 | Co | <0.2 |
| 17 | Terbium Oxide | 0.53 | 2.54 | — | — |
| 18 | Zirconium Oxide | 0.56 | 2.20 | — | — |

[a]Wt. % TBHP left in effluent determined by iodometric titration.
[b]Metal contents in effluent determined by atomic adsorption analysis.

EXAMPLES 19-22

These examples will illustrate the preparation of the unique cobalt borate on titanium dioxide catalysts.

EXAMPLE 19

Titanium dioxide pellets (50 ml, $\frac{1}{8}''$, Norton) were treated with 10% ammonium borate (in demineralized water). The pellets were allowed to stand about 15 minutes with occasional stirring. The aqueous solution was decanted and the pellets dried at room temperature for a few minutes. The pellets were then treated with 10% cobalt nitrate (in demineralized water). The pellets were again let stand for 15 minutes with occasional stirring. The pellets were dried for 40 hours and a small amount powdered and analyzed for percent cobalt and percent boron by atomic adsorption. The following results were obtained.

Boron, wt. %: 0.336
Cobalt, wt. %: 0.68

EXAMPLE 20

The procedure was the same as that for Example 19 except that 10% sodium borate was used instead of 10% ammonium borate. The following results were obtained.

Boron, wt. %: 0.361
Cobalt, wt. %: 0.677

EXAMPLE 21

The procedure was the same as that for Example 20 except that phosphoric acid treated pellets were used. The following results were obtained.

Boron, ppm: <500
Cobalt, wt. %: 0.222

EXAMPLE 22

The procedure was the same as that for Example 20 except that the pellets were treated only with 10% cobalt nitrate. The following results were obtained.

Cobalt, wt. %: 0.380

EXAMPLE 23

A cobalt borate catalyst from Example 20 which contained 0.677% cobalt and 0.36% boron was charged to a 25 cc stainless steel tubular reactor and TBA pumped through for 1-2 hours at 500 psi. A dilute solution of TBHP (2.0 wt. %) in TBA was then pumped through the reactor at 30 cc/hour. The solution was pumped through the reactor at the desired temperature for several hours and then a 20-25 ml sample was taken for analysis. The results are shown below.

| Temperature °C. | Wt. % TBHP by Titration | ppm Cobalt by Atomic Adsorption |
|---|---|---|
| 140 | <0.03 | <0.2 |
| 120 | <0.03 | <0.2 |
| 100 | 0.062 | <0.2 |
| 80 | 0.081 | <0.2 |

Gas chromatography analysis of the reactor effluent from the 140° C. run showed 0.43% acetone and 99.14% TBA along with minor amounts of other products. This indicated that most of the TBHP decomposed to TBA. Percent boron was 68 ppm, indicating that only small amounts had leeched.

EXAMPLE 24

The procedure was the same as that for Example 23 except that different flow rates were used.

| Temperature °C. | Space Vel., cc/hr | TBHP$^a$, wt. % | ppm$^b$ Cobalt | Wt. %$^c$ TBA | Wt. %$^c$ Acetone |
|---|---|---|---|---|---|
| 120 | 69.8 | <0.04 | <0.2 | 98.63 | 0.55 |
| 141 | 69.8 | 0.05 | — | 98.68 | 0.60 |
| 139 | 93.5 | 0.05 | — | 98.65 | 0.61 |
| 120 | 93.5 | 0.07 | — | 99.39 | 0.071 |

Many modifications may be made in the method of this invention without departing from the spirit and scope thereof which are defined only in the appended claims. For example, the catalyst proportions and reaction temperature could be modified by one skilled in the art to optimize this decomposition technique.

We claim:

1. A method for the decomposition of an organic hydroperoxide which comprises contacting a liquid solution containing an organic hydroperoxide with a cobalt borate insoluble catalyst at a temperature in the range of 50° to 250° C. to give an effluent substantially free of the organic hydroperoxide.

2. The method of claim 1 in which the concentration of organic hydroperoxide in the liquid solution ranges from 0.1 to 10 wt. % and the concentration of organic hydroperoxide in the effluent is equal to or less than 0.2 wt. %.

3. The method of claim 1 in which the organic hydroperoxide is t-butyl hydroperoxide and t-butyl alcohol is also present in the liquid solution.

4. The method of claim 1 in which the decomposition reaction is conducted at a temperature between 80° and 120° C.

5. The method of claim 1 in which the catalyst concentration ranges from 0.1 to 10 wt. %.

6. A method for the decomposition of t-butyl hydroperoxide in a solution with t-butyl alcohol which comprises contacting a liquid solution containing t-butyl hydroperoxide and t-butyl alcohol with an insoluble catalyst selected from the group consisting of cobalt borate alone and cobalt borate on a titanium dioxide support, at a temperature in the range of 80° to 120° C. to give an effluent substantially free of t-butyl hydroperoxide.

7. The method of claim 6 in which the concentration of t-butyl hydroperoxide in the liquid solution ranges from 0.1 to 10 wt. % and the concentration of t-butyl hydroperoxide in the effluent is equal to or less than 0.2 wt. %.

8. The method of claim 6 in which the catalyst concentration ranges from 0.1 to 10 wt. %.

9. A method for the decomposition of t-butyl hydroperoxide in a solution with t-butyl alcohol which comprises contacting a liquid solution containing 0.1 to 10 wt. % t-butyl hydroperoxide in t-butyl alcohol with 0.1 to 10 wt. % of an insoluble catalyst selected from the group consisting of cobalt borate alone and cobalt borate on a titanium dioxide support, at a temperature in the range of 80° to 120° C. to give an effluent having a t-butyl hydroperoxide concentration of equal to or less than 0.2 wt. %.

* * * * *